(12) United States Patent
Escala

(10) Patent No.: US 11,768,197 B1
(45) Date of Patent: Sep. 26, 2023

(54) RAPID FERTILITY AND HEALTH INDICATOR

(71) Applicant: Eggschain, Inc., Austin, TX (US)

(72) Inventor: Wei Escala, Austin, TX (US)

(73) Assignee: Eggschain, Inc., Austin, TX (US)

( * ) Notice: Subject to any disclaimer, the term of this patent is extended or adjusted under 35 U.S.C. 154(b) by 0 days.

(21) Appl. No.: 18/126,193

(22) Filed: Mar. 24, 2023

Related U.S. Application Data

(62) Division of application No. 17/842,635, filed on Jun. 16, 2022.

(60) Provisional application No. 63/259,001, filed on Aug. 21, 2021, provisional application No. 63/259,121, filed on Jun. 19, 2021.

(51) Int. Cl.
*G01N 33/53* (2006.01)
*G01N 33/50* (2006.01)
*A61B 10/00* (2006.01)
*G01N 33/68* (2006.01)

(52) U.S. Cl.
CPC ..... *G01N 33/5091* (2013.01); *A61B 10/0058* (2013.01); *G01N 33/689* (2013.01)

(58) Field of Classification Search
CPC .................................................. G01N 33/5091
See application file for complete search history.

(56) References Cited

U.S. PATENT DOCUMENTS

| | | | | |
|---|---|---|---|---|
| 2008/0113045 | A1* | 5/2008 | Rashan | A61P 15/08 424/755 |
| 2012/0301476 | A1* | 11/2012 | Okano | A61P 35/02 424/139.1 |
| 2015/0300932 | A1* | 10/2015 | Schaff | G01N 1/4077 435/288.6 |
| 2022/0334129 | A1* | 10/2022 | Kringelum | A61P 31/04 |

* cited by examiner

*Primary Examiner* — Albert M Navarro
(74) *Attorney, Agent, or Firm* — Frost Brown Todd LLP; Vance Vandrake; Alexander Johnson

(57) ABSTRACT

Methods and devices of determining one or more of a male's likely fertility and health using an indicator are described herein. The indicator can measure one or more or the sperm quantity, sperm quality, and sperm motility. The methods can be regularly repeated to track one or more of likely fertility and health.

12 Claims, No Drawings

RAPID FERTILITY AND HEALTH INDICATOR

CROSS-REFERENCE TO RELATED APPLICATIONS

The present application is a divisional application of U.S. Non-Provisional patent application Ser. No. 17/842,635, filed Jun. 16, 2022, which claims the priority benefit of U.S. Provisional Patent App. Ser. No. 63/259,001, filed Aug. 21, 2021, and U.S. Provisional Patent App. Ser. No. 63/259,121, filed Jun. 19, 2021, each of which are incorporated by reference herein.

TECHNICAL FIELD

The present disclosure relates generally to rapid fertility and health indicators using sperm.

BACKGROUND

Evaluation of men's fertility requires testing of the men's sperm which is traditionally performed in a medical setting at the direction of a doctor. The overall health of men is also traditionally measured at a doctor's office using a variety of tests such as heart rate, weight, body dimensions, blood pressure, blood tests, cholesterol, hormone levels, and sleep quality among numerous other tests and measurements. However, men are much more unlikely to visit a medical professional than woman. Accordingly, despite the benefits of visiting a doctor, men are unlikely to monitor their overall fertility and health as much as ideal. As such, there is a long felt need for testing and preventive care for men that can detect issues prior to visiting a medical professional and which can be more convenient or potentially more frequently performed.

SUMMARY

According to one embodiment, a method of evaluating the fertility and health of a male includes the steps of depositing a sperm sample on an indicator, measuring one or more of the sperm quantity, sperm quality, and sperm motility and determining one or more of the likely fertility and health of the male using the one or more of the sperm quantity, sperm quality, and sperm motility.

According to another embodiment, an indicator for evaluating the likely fertility and health of a male includes a collection surface for receiving semen; and one or more complimentary amino acids, peptide fragments, and reagents to measure one or more proteins and antibodies contained in the semen. The indicator determines one or more of the sperm quantity, sperm quality, and sperm motility in the semen.

DETAILED DESCRIPTION

The present disclosure generally describes devices and methods to measure and indicate the likely fertility and health of a human male using their semen and sperm. The devices and methods described herein can provide a simple and fast measurement of the man's likely fertility and overall health before requiring complicated measurements, specialized equipment, or interpretation by a doctor or other medical personnel. Generally, the devices and methods described herein measure the likely fertility and health of a human male by measuring one or more of the quantity, quality, and motility of sperm using an easy to use indicator.

As will be described further herein, the indicator can vary widely in form including, for example, as a self-contained stick or swab, as a card or booklet, as a cloth, as a container, as a condom or other contraceptive tool, or as a combination of such items. For example, in certain embodiments, the easy to use indicator can include both a swab and a card or booklet. In certain embodiments, the indicator can be a stick with a cotton swab on one end.

Generally, the indicator can measure one or more of sperm quantity, sperm quality, and sperm motility by measurement of various antibodies and proteins contained within semen. For example, the indicator can measure the quantity of sperm by measuring the number or concentration of proteins located on the surface of sperm. Sperm quality can similarly be measured through the presence of antibodies and proteins contained within semen, or on sperm, by measurement of the amount of live sperm and sperm motility, or by other methods. In certain embodiments, acrosin can be used to measure sperm quality. Acrosin is an enzyme produced by the body to breakdown sperm by attacking the zona pellucida.

To measure the antibodies and proteins, the indicators can include complimentary peptide fragments that can bind to antibodies or sperm cells contained within a semen sample. The binding can be used to determine one or more of sperm quantity, sperm quality, and sperm motility either directly after binding or after activation with, for example, an additional chemical or UV light.

The indicator can indicate one or more sperm quantity, sperm quality, and sperm motility in various ways such as through a color change, the presence of an indicator at a particular location, or other visual or physical change. For example, in certain embodiments, the indicator can display different colors for each of sperm quantity, sperm quality, and sperm motility with the resulting composite color indicating the levels of each. In such embodiments, a lookup table could then provide levels for each of sperm quantity, sperm quality and/or sperm motility. In other embodiments, a card or booklet can include indicators at differing locations for the quantity, quality, and/or motility of the sperm. As can be appreciated, additional colors or location indicators can be included in certain embodiments to convey more information. In embodiments using a container, condom, or the like, the volume of semen can additionally be measured.

In certain embodiments, the indicator can be a swab, a stick, a card, a container, a contraceptive tool, or a booklet where the semen sample is directly applied to the indicator. In such embodiments, the indicator can be pre-impregnated with reagents, compounds with complimentary amino acid and peptide sequences, and the like to bind to various antibodies and proteins contained within a semen sample. The semen can be applied at a single location or can be applied at multiple locations. For example, a stick may change color to indicate one or more of sperm quality, quantity, or motility while a card may ask for a sample at various locations on the card or booklet and then display results at each of the various locations.

As can be appreciated, the indicator can also be electronically read in certain embodiments. In such embodiments, the indicator can be placed in, or otherwise read by, an electronic reader which can automatically interpret the results and provide the results to the user with accompanying information. In certain embodiments, the electronic reader can be a cellphone. In other embodiments, the electronic reader can be an independent device. In certain embodiments, the electronic reader can further electronically transmit information to a healthcare provider.

In certain embodiments, the indicator can be a chromatographic indicator. In a chromatographic process, a semen coated swab can be diluted into a suitable carrier and extraction buffer, and then the carrier and extraction buffer can be transferred onto a chromatographic card or booklet. The carrier and extraction buffer containing the semen sample can then chromatographically travel along the card or booklet to provide information about one or more of sperm quantity, sperm quality, and sperm motility. Such an indicator can provide binary results indicating a certain threshold of the one or more of sperm quantity, sperm quality, and sperm motility while in other embodiments, quantitative results can be provided by having multiple indicator lines on the indicator.

In various embodiments, the indicators can further include additional components. For example, in certain embodiments, the reagents, compounds with complimentary amino acid and peptide sequences, etc., can be separately provided and can be combined with the swab in a provided sample holder or test tube. In certain embodiments, a separate collection container can also be provided to measure the volume of semen.

Generally, the indicators can measure the one or more of the sperm quantity, sperm quality, and sperm motility rapidly. For example, in certain embodiments, the indicator can measure the one or more of the sperm quantity, sperm quality, and sperm motility in about 2 hours or less, about an hour or less, in about 30 minutes or less, in about 15 minutes, in about 5 minutes or less, or in about 1 minute. As can be appreciated, such timeframes facilitate easy use of the indicators and can encourage their use.

As can be appreciated, the indicators described herein are both easy to use and cheap to manufacture. Such features enable the indicators to be easily used at home and then disposed of with minimal training and cost. Sequential and/or regular testing over longer durations of time are also enabled by the low cost and easy to use design.

The indicators described herein can inform a male whether they are likely to be fertile and can also provide information about their likely overall health by comparing the sample against known fertile and healthy metrics. Specifically, a healthy sperm sample typically has a volume of about 1.5 ml to about 7.6 ml, a concentration of about 15 million to about 259 million sperm per ml, a total number of sperm per ejaculate of about 39 million to about 928 million, a sperm motility percentage ranging from about 40% to about 81% with 32% to about 75% exhibiting progressive motility, a normal morphology of about 4% to about 48%, with about 58% to 92% being live sperm. The indicators described herein can indicate whether the sperm is within one or more of such bounds or can provide a direct measurement of such values.

For example, in certain embodiments, the indicators can determine whether the concentration of sperm is within about 15 million to about 259 million per ml and whether about 40% to about 81% of the sperm exhibit motility. A sample having such a concentration of sperm and amount exhibiting motility would indicate that the male has a healthy sperm sample and is likely to be fertile. In certain embodiments, the frequency and volume of the man's ejaculate can further be used to indicate quality of the sperm sample and the likely fertility of the man.

In addition to indicating whether a male is likely fertile or infertile, the indicators described herein can also or alternatively provide an overall assessment of men's health and vitality. For example, an unhealthy sperm sample can indicate elevated nicotine levels, elevated stress, new changes in exercise, life changing events, heart issues, vascular issues, exposure to various harmful chemicals, obesity, binge drinking, lack of sleep, and/or blood pressure issues.

In certain embodiments, the methods and devices described herein can provide further detail about a man's likely health. For example, excessive drinking (more than 40 units of alcohol per week) is associated with a 33% lower sperm count and a 51% decrease in healthy sperm than a similar male who drinks between one and five units per drink. As used herein, healthy sperm means sperm having a forward motility progression of at least about 25 micrometers per second. In embodiments providing quantitative details, the indicators described herein can thus provide an indication that the male is drinking to an excessive degree and is causing detrimental damage to his health and vitality. Similarly, lack of sleep is associated with a 1.6% increase in damaged sperm.

An unhealthy sperm sample as determined by the indicator can further indicate nerve damage in certain embodiments. As can be appreciated, damage to the nerves in the central nervous system, the spinal cord, or the bladder can impact semen flow leading to poorly performing semen samples. In particular, diabetes is significantly associated with nerve damage that causes ejaculation issues including retrograde ejaculation causing some or all of the ejaculate to go back into the bladder. Poor indicator results can therefore be used as an indication of nerve damage.

In certain embodiments, poor results from the indicator can also, or alternatively, indicate that the male suffers from prostate conditions. For example, both enlarged prostates and prostate cancer can affect ejaculation and decrease the quality of a sperm sample.

As can be appreciated, unhealthy sperm samples as determined by the indicators described herein can indicate yet other poor health outcomes with sperm quality and quantity decreasing with age, certain medications, and radiation exposure.

The methods and devices described herein can thus provide a rapid test to indicate a man's likely fertility and health that can be performed alone and in the comfort of their dwelling. A healthy sample can indicate that the male is likely fertile and generally healthy and not suffering from poor dietary consumption, excessive alcoholic consumption, taking recreational or prescription drugs, suffering from nerve or prostate damage, or other hard to detect damage.

Conversely, an unhealthy sample can indicate that the male is not healthy. In certain embodiments, the indicators described herein can indicate the cause while in other embodiments, the unhealthy sample can just provide an indicator that the male is unhealthy and see a doctor.

In certain embodiments, the methods and devices described herein can be particularly useful for serial and/or regular testing. Because the indicators are cheap and easy to administer, they can be regularly used as part of a proscribed monitoring system to enable a male to see if their fertility or health changes. Being fast and easy to use, regular use can provide information about changes in lifestyle or exposure to dangerous conditions. In such embodiments, the indicators can be used on a predetermined, or as needed, schedule. For example, the indicators can be used every 2 weeks, every month, etc.

In certain embodiments, the indicator can be a condom that can be used during normal sexual activity. As can be appreciated, the use of such condoms as indicators can encourage use and can immediately convey information to the user about one of more of their likely fertility and health. In such embodiments, the indicator can otherwise be a functional condom that meets all required contraceptive requirements expected of condoms.

Alternatively, in certain embodiments, the indicator can have the design of a condom but without the contraceptive requirements expected of a condom. For example, the indicator can visually appear to be a condom but have one or more openings near the tip to let semen pass through. Such indicators can provide an indication after sexual intercourse whether the male is likely to be fertile while also allowing for contraception to occur if the male is fertile. Such indicators can be useful for couples attempting to have kids.

In certain embodiments, the male being evaluated by the devices and methods described herein can be instructed to abstain from sex or masturbation for a pre-determined period of time to normalize the results of the indicators. For example, in certain embodiments, the male can be instructed to forego sex or masturbation for about a week before evaluation. In yet other embodiments, specific durations of time between the last instance of sex or masturbation before the evaluation can be specified to evaluate sperm recovery times.

The dimensions and values disclosed herein are not to be understood as being strictly limited to the exact numerical values recited. Instead, unless otherwise specified, each such dimension is intended to mean both the recited value and a functionally equivalent range surrounding that value.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross-referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in the document shall govern.

The foregoing description of embodiments and examples has been presented for purposes of description. It is not intended to be exhaustive or limiting to the forms described. Numerous modifications are possible in light of the above teachings. Some of those modifications have been discussed and others will be understood by those skilled in the art. The embodiments were chosen and described for illustration of various embodiments. The scope is, of course, not limited to the examples or embodiments set forth herein, but can be employed in any number of applications and equivalent articles by those of ordinary skill in the art. Rather it is hereby intended the scope be defined by the claims appended hereto.

It should be understood that certain aspects, features, structures, or characteristics of the various embodiments can be interchanged in whole or in part. Reference to certain embodiments mean that a particular aspect, feature, structure, or characteristic described in connection with certain embodiments can be included in at least one embodiment and may be interchanged with certain other embodiments. The appearances of the phrase "in certain embodiments" in various places in specification are not necessarily all referring to the same embodiment, nor are certain embodiments necessarily mutually exclusive of other certain embodiments. It should also be understood that the steps of the methods set forth herein are not necessarily required to be performed in the orders described, and the order of the steps of such methods should be understood to be merely exemplary. Likewise, additional steps can be included in such methods, and certain steps may be omitted or combined, in methods consistent with certain embodiments.

What is claimed is:

1. An indicator for evaluating the likely fertility and health of a male comprising:
   a collection surface for receiving a semen sample; and
   one or more reagents to measure one or more proteins and antibodies contained in the semen sample;
   wherein the indicator determines one or more of sperm quantity, sperm quality, and sperm motility in the semen sample; and
   wherein the indicator includes a condom that allows the semen sample to pass through an opening in the condom.

2. The indicator of claim 1, wherein the indicator exhibits a visual change to indicate one or more of the sperm quantity and sperm quality in the semen.

3. The indicator of claim 1, wherein the sperm motility comprises the percentage of sperm in the semen sample having motility and the average motility rate.

4. The indicator of claim 1, wherein the indicator further determines the percentage of live sperm in the semen sample.

5. The indicator of claim 1, wherein the indicator further determines if the male is afflicted with one or more of excess alcohol consumption, nerve damage, heart damage, vascular damage, radiation exposure, diabetes, insufficient sleep, or prostate indications.

6. The indicator of claim 5, wherein excessive alcohol consumption is indicated by the semen sample containing 30 million sperm or less and about 50% of less of sperm in the semen sample exhibiting motility.

7. The indicator of claim 1, wherein the one or more of the sperm quantity, sperm quality, and sperm motility is determined without interpretation by a doctor or other medical personnel.

8. The indicator of claim 1, wherein the one or more reagents bind to antibodies or sperm cells contained within a semen sample to create a bound semen sample.

9. The indicator of claim 8, wherein the bound semen sample is activatable with the addition of an additional chemical or by activation with UV light.

10. The indicator of claim 1, wherein the indicator can measure the one or more of the sperm quantity, sperm quality, and sperm motility in less than about 2 hours.

11. The indicator of claim 10, wherein the indicator can measure the one or more of the sperm quantity, sperm quality, and sperm motility in less than about 30 minutes.

12. The indicator of claim 11, wherein the indicator can measure the one or more of the sperm quantity, sperm quality, and sperm motility in less than about 5 minutes.

* * * * *